United States Patent [19]

Pepper

[11] Patent Number: 5,609,596
[45] Date of Patent: Mar. 11, 1997

[54] GUIDE ROD HOLDER FOR MANIPULATING SURGICAL WIRES AND PINS

[75] Inventor: John R. Pepper, Germantown, Tenn.

[73] Assignee: Smith & Nephew Richards Inc., Memphis, Tenn.

[21] Appl. No.: 401,150

[22] Filed: Mar. 9, 1995

[51] Int. Cl.$^6$ .................................................. A61B 17/82
[52] U.S. Cl. ................................................ 606/103; 606/74
[58] Field of Search .............................. 606/103, 74, 86, 606/205, 206, 148, 149, 150

[56] References Cited

U.S. PATENT DOCUMENTS

| | | |
|---|---|---|
| 5,052,243 | 10/1991 | Tepic . |
| 5,116,340 | 5/1992 | Songer et al. ........................ 606/103 |
| 5,284,487 | 2/1994 | Hartmeister ......................... 606/205 |
| 5,395,374 | 3/1995 | Miller et al. ......................... 606/74 |

*Primary Examiner*—Guy V. Tucker
*Attorney, Agent, or Firm*—Pravel, Hewitt, Kimball & Krieger

[57] ABSTRACT

A surgical guide rod holder is provided for holding guide rods, surgical pins, bone pins, trochars and the like during orthopedic surgery procedures. The apparatus has a frame with a handle and a barrel. The barrel has two spaced apart supports that hold the pin or rod. A multi-link assembly is operated by a trigger. The multi-link assembly moves between gripping and releasing positions when the surgeon rotates the trigger. The multi-link assembly includes a link member that presses laterally against the pin or rod during gripping, forcing the pin against the barrel. A turnbuckle adjusts the multi-link assembly to provide greater/lesser "bite" for holding the rod or pin, or for allowing holding of pins of different sizes.

9 Claims, 3 Drawing Sheets

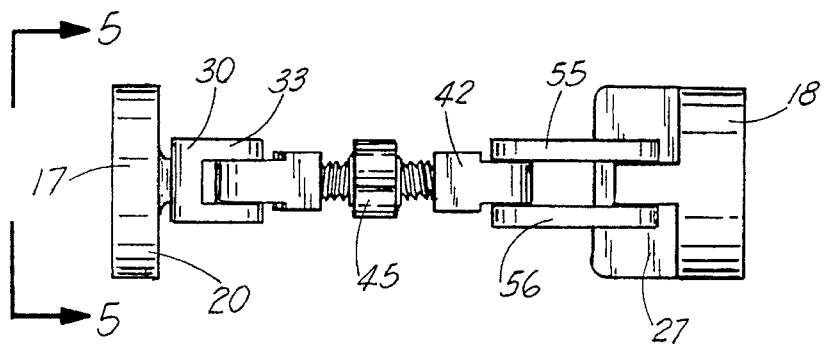
FIG. 4
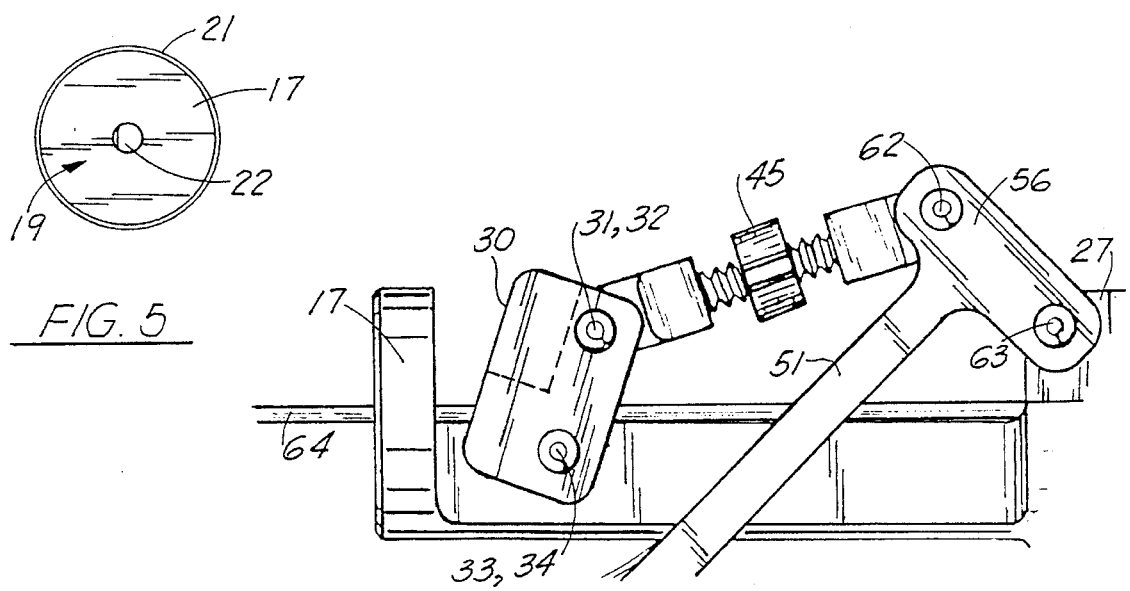
FIG. 5
FIG. 6
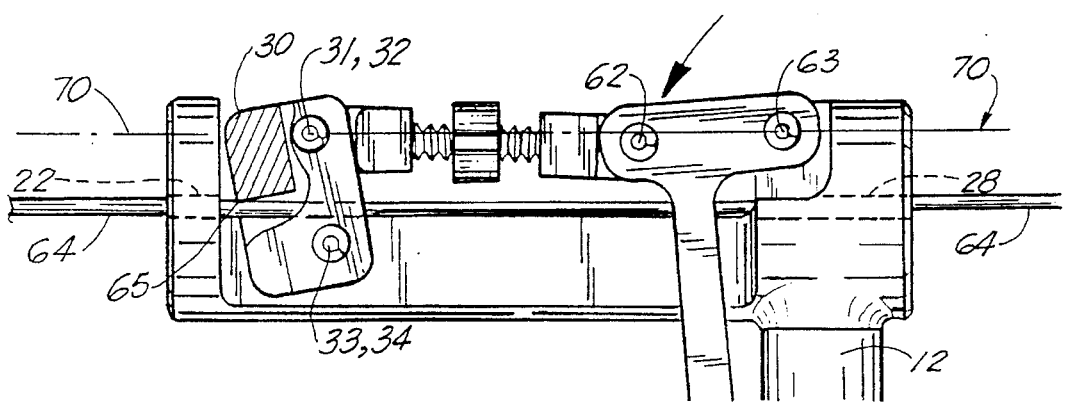
FIG. 7

GUIDE ROD HOLDER FOR MANIPULATING SURGICAL WIRES AND PINS

BACKGROUND OF THE INVENTION

1. Field of the Invention

The present invention relates to orthopedic surgical instruments and more particularly to an improved instrument for holding and manipulating wires and pins that are used in orthopedic surgical procedures such as the Ilizarov surgical procedure, intramedullary rod placement, and like surgical procedures. Even more particularly, the present invention relates to an improved guide rod and pin holder that can interchangeably support guide rods and surgical pins of differing diameters, wherein an adjustable four bar linkage is operated by a trigger to pinch the guide rod. The degree to which the rod is indented depends upon the setting of a turnbuckle that is part of the four bar linkage.

2. General Background

Various orthopedic surgical procedures require the use of various types of guide rods and surgical pins. For example, in the placement of intramedullary rods and recon nails, guide rods are first placed by the surgeon to define the path that is then traveled by the implant (such as an intramedullary nail).

When a surgeon affixes an Ilizarov type fixation system to a patient, a plurality of bone pins are inserted transversely through the patient's bone above and below a fracture or bone defect. These procedures require that the surgeon be able to easily and effectively hold and manipulate the wires and pins.

Patents have issued that relate to linkage systems that are part of an instrument. These include for example, the Harthmeister U.S. Pat. No. 5,284,487 and the Tepic U.S. Pat. No. 5,052,243.

SUMMARY OF THE INVENTION

The present invention provides a guide rod holder for supporting and manipulating a surgical guide wire, surgical pin, bone pin or the like.

The apparatus includes an instrument frame having a handle for gripping the frame and a trigger movably mounted with respect to the frame.

A barrel section of the frame is provided for receiving and holding a surgical guide wire or bone pin, the barrel having a distal end and a proximal end. The barrel has supports, each with a channel that receives the wire during use.

A multi-link assembly is disposed adjacent the barrel section, the assembly including a plurality of links that are movable between wire engaging or grasping, and wire releasing positions.

The links pinch and indent the wire with a wire engaging surface in the grasping position. The links are spaced away from the wire in the releasing position.

The guide rod is held with such force that by a gripping surface that a small indentation can be formed on the rod. However, the degree to which the rod is indented depends on the setting of a turnbuckle. The guide rod may be held without damage if the turnbuckle is set for a very light hold. There is a great mechanical advantage provided with the trigger of the apparatus of the present invention in that the force on the handle or trigger is multiplied by approximately 75 times at the actual gripping or pinching surface.

The apparatus of the present invention can be operated with one hand unlike current prior art Jacob's chuck devices, thus reducing the time needed to manipulate the guide rod during surgery.

With the present invention, there is often a need to hammer on a guide rod holding device during surgery. This frequently breaks Jacob's chuck type devices, usually during the extraction of a nail after the threads in the nail get stripped. With the present invention, the instrument frame can be hammered on either end surface without damage to the instrument.

With the present invention, a grasping position rotates the linkage about a pivot below a reference line and locks it into place, not requiring any substantial force from the surgeon's hand.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 4 is a partial top view of the preferred embodiment of the apparatus of the present invention illustrating the linkage portion thereof;

FIG. 5 is an end view taken along lines 5—5 of FIG. 4;

FIG. 6 is a side fragmentary view of the preferred embodiment of the apparatus of the present invention illustrating the linkage in the releasing position;

FIG. 7 is a side fragmentary view of the preferred embodiment of the apparatus of the present invention illustrating the linkage in the grasping position.

DETAILED DESCRIPTION OF THE PREFERRED EMBODIMENT

Figure 1:
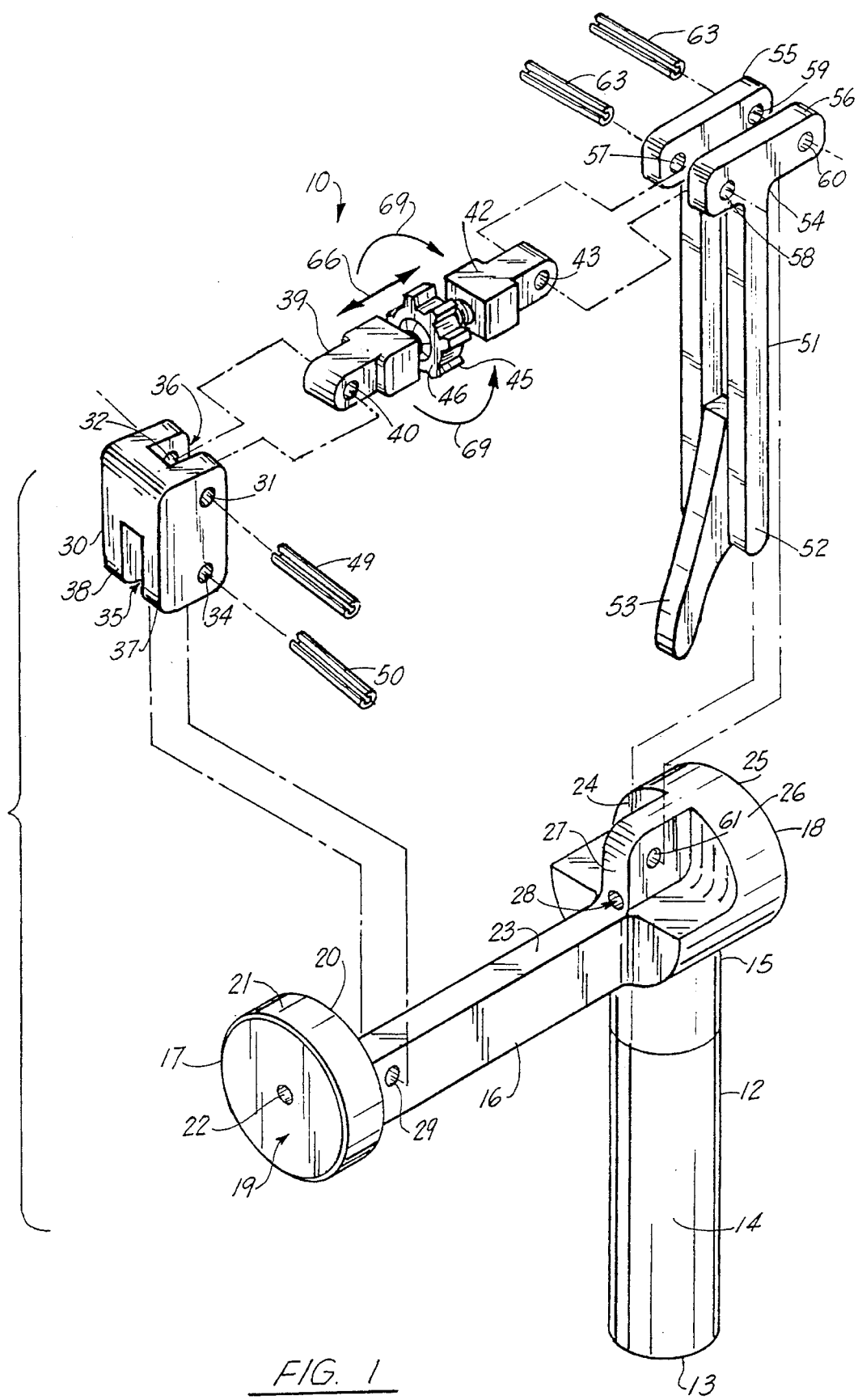
FIG. 1 is a perspective exploded view of the preferred embodiment of the apparatus of the present invention.

FIG. 1 shows the preferred embodiment of the apparatus of the present invention designated generally by the numeral 10. Guide rod holder 10 includes an instrument body 11 that has a handle portion 12 and the barrel portion 16.

The handle 12 includes a proximal 15 and distal ends 13 and provides a generally cylindrical gripping surface 14. The proximal end 15 of handle 12 forms an integral connection with the horizontally extending barrel 16 as shown in FIG. 1.

A pair of supports 17, 18 are positioned at the distal and proximal ends of the horizonal barrel 16. At the distal end of barrel 16 there is provided a generally circular front support 17. At the proximal end of barrel 16 is provided rear support 18.

Figure 2:
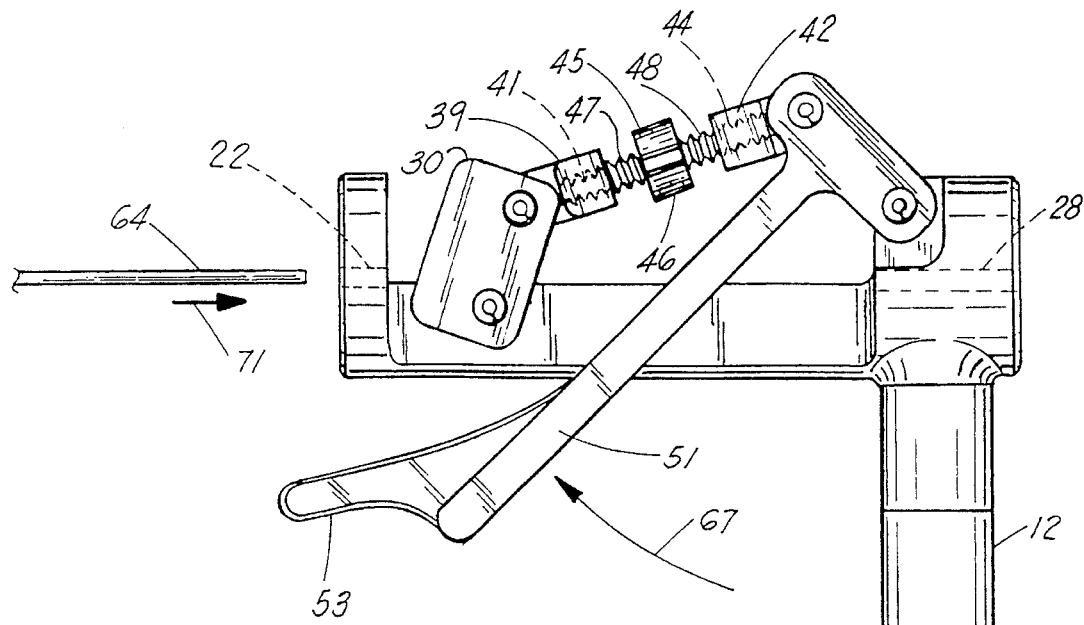
FIG. 2 is an elevational view of the preferred embodiment of the apparatus of the present invention shown in the releasing position.
Figure 3:
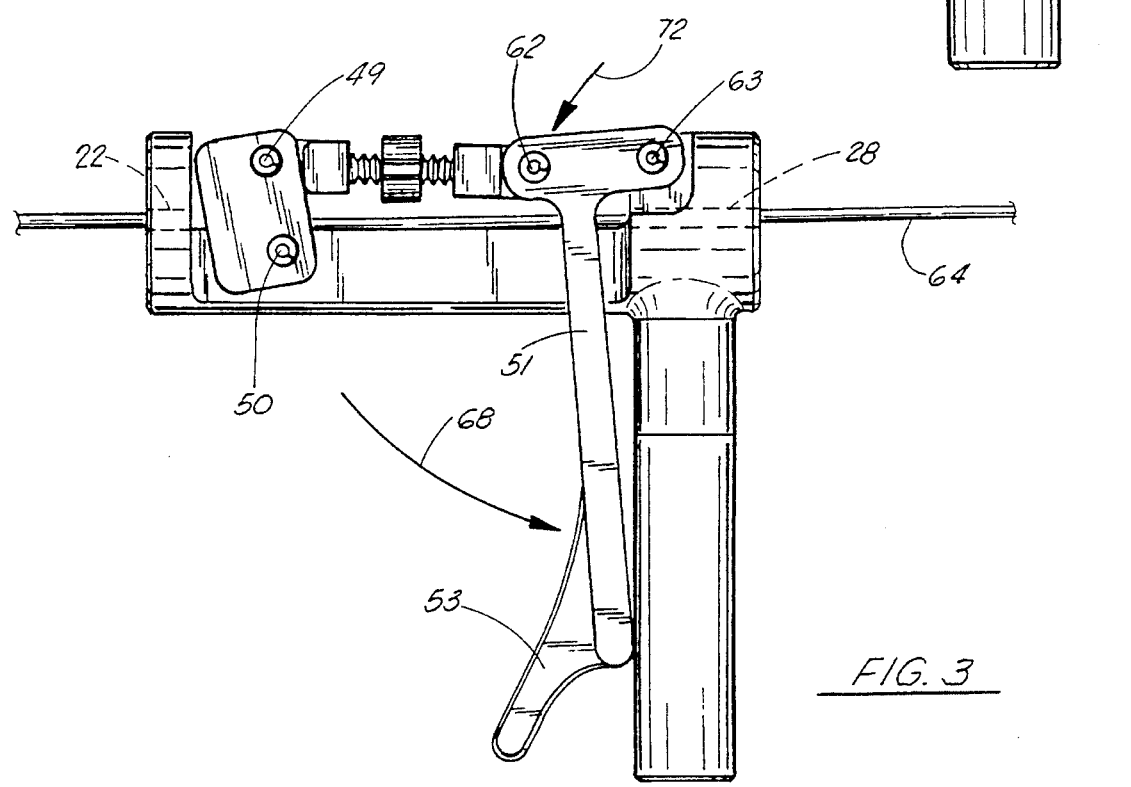
FIG. 3 is an elevational view of the preferred embodiment of the apparatus of the present invention shown in the grasping position.

The front support 17 has a pair of opposed, parallel circular surfaces 19, 20 and a peripheral surface 21. If desired, the surface 19 can be hammered, even when a guide rod 64 is gripped. An open ended generally cylindrically shaped channel 22 extends between the front circular surface 19 and the rear circular surface 20. The open-ended channel 22 receive a guide wire to be supported by the apparatus 10 during use as will be described more fully hereinafter. A second generally cylindrically shaped channel 28 extends through rear support 18. Channel 28 also receives a guide wire or pin during use. Each of the channels 22, 28 is generally cylindrical, providing a central longitudinal axis. Each channel axis falls along a common axial line so that a guide wire inserted through the opening 22 also aligns with and registers in the opening 28 as shown in FIGS. 2 and 3.

The upper surface 23 of barrel 16 is positioned below the guide wire and the two openings 22, 28 during use. This allows the guide wire to be slightly pinched when the apparatus 10 is placed in the grasping position.

Rear support 18 has a pair of opposed surfaces 24, 25 and a peripheral surface 26. The rear surface 25 can be hammered if desired to assist in removal or insertion of a guide rod 65. The rear support 18 provides a vertically and horizontally extending flange 27 to which linkage members are attached as will be described more fully herein.

A transverse opening 29 is provided near the distal end of barrel section 16. The transverse opening 29 accepts a pin 50 that also extends through openings 33, 34 of link member 30.

As shown in FIG. 1, the link member 30 has a pair of upper openings 31, 32 and a pair of lower openings 33, 34. The upper openings 31, 32 are shaped, configured and aligned to accept pin 49. The lower openings 33, 34 are similarly configured and aligned to accept the pin 50. A horizonal slot 35 and a vertical slot 36 are provided on link member 30. The slots 35, 36 communicate as shown. Horizontal slot 35 registers over barrel member 16. The vertical slot 36 accepts link member 39. The slots 35 and 36 are positioned between spaced apart flanged members 36, 37 of link 30.

The link member 39 includes a transverse opening 40 and an internally threaded longitudinal opening 41 as shown in FIG. 2. The transverse opening 40 registers along an axial line with the openings 31, 32 of link member 30. In this fashion, transverse pin 49 extends through opening 31, opening 40 and opening 32 upon assembly.

A second link 42 is similar in configuration to the link 39, but faces in an opposite direction as shown in FIG. 1. The link 42 likewise, provides a transverse opening 43 and a longitudinally extending internally threaded opening 44 (see FIG. 2).

Turnbuckle 45 engages internally threaded openings 41, 44 as shown in FIG. 1. Turnbuckle 45 is comprised of a knob 46 and externally threaded rods 47, 48 which have threads that are in opposite directions. The knob 46 and threaded rods 47, 48 are integral. Therefore, when the user rotates the knob 46 as shown by the curved arrow 69 in FIG. 1, the link members 39, 42 move together/apart depending upon the direction of rotation. The extension or contraction of link members 39, 42 with respect to one another is shown by the straight arrow 66 in FIG. 1.

A lever arm 51 attaches to the link member 42 and to rear support 18 at flange 27. Lever arm 51 has a distal end 52 with trigger 53. Proximal end 54 of lever arm 51 has a pair of spaced apart flanges 55, 56. Each of the flanges 55, 56 provides openings for receiving transverse pins 62, 63. The flange 55 has transverse opening 57, 59. The flange 56 has transverse openings 58, 60. Transverse pin 62 extends through opening 57 of flange 55 through opening 43 of link 42, and the through opening 58. Transverse pin 63 extends through opening 59, then transverse opening 61 of flange 27 on support 18 and then through openings 60.

In FIGS. 2–3, operation of the apparatus 10 of the present invention is illustrated. In FIG. 2, the apparatus 10 is shown in a "releasing" position with the lever arm 51 having been rotated away from handle 12 using trigger 53 as shown by curved arrow 67.

In FIG. 3, the "engaged" or gripping position is shown. The curved arrow 68 illustrates a rotation of lever arm 51 into a position adjacent handle 12. In FIG. 3, guide wire 64 is shown having been inserted through channels 22, 28. Once the guide wire 64 is extend through both channels 22 and 28 (see arrow 71, FIGS. 2 and 3), the user then rotates lever arm 51 in the direction of arrow 68 using trigger 53. This produces a rotation of pin 62 and lever arm 51 pin about pin 63 (see arrows 68, 72) which function as a pivot. This action by moving 39, 45, 42 also rotates pin 49 relative to pin 50, the latter pin 50 defining a pivot.

When the user rotates the lever arm 51 into the engaged or gripping position of FIG. 3, the link member 30 rotates about pin 50 so that the wire engaging surface 65 engages the guide wire 64. In FIG. 7, when the surface 65 engages the wire 64, the wire is pressed firmly against the upper surface 23 of barrel 16. In this position, the wire 64 is held by 28 and the engaging surface 65 of link member 30, pinching wire 64 against surface 23. Further, the pin 62 drops to a position below the reference line 70 that extends along a straight line between pin 49 and pin 62. This action actually "snaps" the linkage into the position of FIG. 7, as the linkage defined by members 39, 47, 48 and 42 is slightly longer than the distance between pins 49 and 63.

By rotating the knob 46 of turn buckle 45, the user can adjust the distance between transverse pin 49 and transverse pin 62 to achieve a desired geometry. The degree of bite that is generated between the surface 65 and the side walls of upper surface 23 of barrel 16 is achieved upon selected rotation of the lever 51 into the engaged or grasping position of FIG. 3.

The following table lists the parts numbers and parts descriptions as used herein and in the drawings attached hereto.

| PARTS LIST | |
|---|---|
| Part Number | Description |
| 10 | guide rod holder |
| 11 | instrument body |
| 12 | handle |
| 13 | distal end |
| 14 | cylindrical gripping surface |
| 15 | proximal end |
| 16 | horizontal barrel |
| 17 | front support |
| 18 | rear support |
| 19 | circular surface |
| 20 | circular surface |
| 21 | peripheral surface |
| 22 | open ended channel |
| 23 | flat surface |
| 24 | surface |
| 25 | circular surface |
| 26 | peripheral surface |
| 27 | flange |
| 28 | open ended channel |
| 29 | transverse opening |
| 30 | link |
| 31 | transverse opening |
| 32 | transverse opening |
| 33 | transverse opening |
| 34 | transverse opening |
| 35 | horizontal slot |

-continued

PARTS LIST

| Part Number | Description |
| --- | --- |
| 36 | vertical slot |
| 37 | flange |
| 38 | flange |
| 39 | link |
| 40 | transverse opening |
| 41 | internally threaded opening |
| 42 | link |
| 43 | transverse opening |
| 44 | internally threaded opening |
| 45 | turnbuckle |
| 46 | knob |
| 47 | externally threaded rod |
| 48 | externally threaded rod |
| 49 | transverse pin |
| 50 | transverse pin |
| 51 | lever arm |
| 52 | distal end |
| 53 | trigger |
| 54 | proximal end |
| 55 | flange |
| 56 | flange |
| 57 | transverse opening |
| 58 | transverse opening |
| 59 | transverse opening |
| 60 | transverse opening |
| 61 | transverse opening |
| 62 | transverse pin |
| 63 | transverse pin |
| 64 | guide wire |
| 65 | wire engaging surface |
| 66 | arrow |
| 67 | curved arrow |
| 68 | curved arrow |
| 69 | curved arrow |
| 70 | reference line |
| 71 | arrow |
| 72 | arrow |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A guide rod holder for supporting and manipulating a surgical guide wire comprising:
   a) an instrument frame having a handle for gripping the frame and a trigger movably mounted on the frame;
   b) a barrel section on the frame for receiving and holding a surgical guide wire, said barrel having a distal end and a proximal end, the barrel having a bore that receives the wire during use;
   c) a multi-link assembly having a length disposed adjacent the barrel section, said assembly including a plurality of links that are movable between grasping and releasing positions, wherein the links abut the wire in the grasping position and wherein the links are spaced away from the wire in the releasing position;
   d) means for biasing the multi-link assembly to the grasping position; and
   e) the multi-link assembly includes an adjuster for adjusting the length of the assembly.

2. The apparatus of claim 1 wherein the handle extends transversely relative to the barrel.

3. The apparatus of claim 1 wherein the multi-link assembly includes a lever that pivots relative to the handle and barrel.

4. The apparatus of claim 1 wherein the adjuster is a turnbuckle.

5. A guide rod holder for supporting and manipulating a surgical guide wire comprising:
   a) an instrument frame having a handle for gripping the frame and a trigger movably mounted on the frame;
   b) a barrel section on the frame for receiving and holding a surgical guide wire, said barrel having a distal end and a proximal end, the barrel having a bore that receives the wire during use;
   c) a multi-link assembly having a length disposed adjacent the barrel section, said assembly including a plurality of links that are movable between grasping and releasing positions, wherein the links abut the wire in the grasping position and wherein the links are spaced away from the wire in the releasing position;
   d) one of the links moving laterally relative to the guide wire to grip the wire;
   e) trigger means for manually moving the multi-link assembly to the grasping position; and
   f) the multi-link assembly includes an adjuster for adjusting the length of the assembly for adjusting the degree of bite that the links grab the wire.

6. The apparatus of claim 5 wherein the handle extends transversely relative to the barrel, and the trigger pivots relative to the barrel.

7. The apparatus of claim 5 wherein the multi-link assembly includes a lever that pivots relative to the handle and barrel.

8. The apparatus of claim 7 wherein the lever rotates to a position aligned with the handle in the grasping position.

9. The apparatus of claim 5 wherein the adjuster is a turnbuckle.

* * * * *